(12) United States Patent
Cass et al.

(10) Patent No.: US 11,944,827 B2
(45) Date of Patent: Apr. 2, 2024

(54) LEAD BODY WITH FLEXIBLE CIRCUITS AND METHOD

(71) Applicant: Heraeus Medical Components LLC, St. Paul, MN (US)

(72) Inventors: Robert R. Cass, St. Paul, MN (US); Paul Noffke, St. Paul, MN (US); Mark A. Hjelle, Fridley, MN (US); Steven E. Scott, Fridley, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 268 days.

(21) Appl. No.: 17/181,117

(22) Filed: Feb. 22, 2021

(65) Prior Publication Data
US 2021/0260384 A1    Aug. 26, 2021

Related U.S. Application Data

(60) Provisional application No. 62/979,564, filed on Feb. 21, 2020.

(51) Int. Cl.
| *A61N 1/375* | (2006.01) |
| *A61N 1/05* | (2006.01) |
| *H01R 11/11* | (2006.01) |
| *H01R 12/77* | (2011.01) |
| *H01R 13/52* | (2006.01) |

(52) U.S. Cl.
CPC ......... *A61N 1/3752* (2013.01); *A61N 1/0534* (2013.01); *H01R 11/11* (2013.01); *H01R 12/771* (2013.01); *H01R 13/5224* (2013.01); *H01R 2201/12* (2013.01)

(58) Field of Classification Search
CPC ...... A61N 1/3752; A61N 1/0534; A61N 1/05; H01R 11/11; H01R 12/771; H01R 13/5224; H01R 2201/12
See application file for complete search history.

(56) References Cited

U.S. PATENT DOCUMENTS

| 4,481,953 | A | 11/1984 | Gold et al. | |
| 5,007,435 | A * | 4/1991 | Doan | A61N 1/056 607/119 |
| 5,928,228 | A | 7/1999 | Kordis et al. | |
| 6,090,104 | A | 7/2000 | Webster, Jr. | |
| 6,256,542 | B1 * | 7/2001 | Marshall | A61N 1/0563 607/119 |

(Continued)

FOREIGN PATENT DOCUMENTS

WO    2016/130713    8/2016

*Primary Examiner* — Jeffrey T Carley
*Assistant Examiner* — Jose K Abraham
(74) *Attorney, Agent, or Firm* — Dicke, Billig & Czaja, PLLC

(57) ABSTRACT

One aspect is a method of forming a lead for implantation. The method includes forming a distal end assembly, forming a proximal end assembly, and forming a flexible circuit coupling the distal end assembly to the proximal end assembly. The distal end assembly, the proximal end assembly and the flexible circuit are formed over an inner member. An outer member is placed over the combination of the distal end assembly, the proximal end assembly and the flexible circuit. The outer member and circuit are fused adjacent the distal end assembly to the proximal end assembly.

13 Claims, 7 Drawing Sheets

(56) References Cited

U.S. PATENT DOCUMENTS

| | | | |
|---|---|---|---|
| 6,757,970 B1* | 7/2004 | Kuzma | A61N 1/0551 600/374 |
| 6,978,185 B2* | 12/2005 | Osypka | A61N 1/056 607/122 |
| 7,555,349 B2 | 6/2009 | Wessman et al. | |
| 7,917,228 B2 | 3/2011 | Wenger | |
| 7,917,229 B2* | 3/2011 | Zarembo | H01R 13/5224 607/116 |
| 8,118,809 B2 | 2/2012 | Paul et al. | |
| 8,147,486 B2 | 4/2012 | Honour et al. | |
| 8,224,457 B2 | 7/2012 | Strandberg et al. | |
| 8,244,373 B1* | 8/2012 | Bauer | H01F 17/00 607/116 |
| 8,996,134 B2 | 3/2015 | Duncan et al. | |
| 9,014,815 B2* | 4/2015 | Yang | A61N 1/05 607/116 |
| 9,226,688 B2 | 1/2016 | Jacobsen et al. | |
| 9,226,689 B2 | 1/2016 | Jacobsen et al. | |
| 9,248,303 B2 | 2/2016 | Yomtov | |
| 9,302,101 B2 | 4/2016 | Wahlstrand et al. | |
| 9,364,662 B2 | 6/2016 | Foster et al. | |
| 9,498,142 B2 | 11/2016 | Hafiz et al. | |
| 9,636,026 B2 | 5/2017 | Hafiz et al. | |
| 9,827,415 B2 | 11/2017 | Stevenson et al. | |
| 9,925,354 B2 | 3/2018 | Scott et al. | |
| 10,207,103 B2* | 2/2019 | Gonzalez | H05K 3/18 |
| 10,556,089 B2* | 2/2020 | Scott | A61B 5/0538 |
| 10,668,273 B2* | 6/2020 | Shah | A61N 1/0529 |
| 11,311,717 B2* | 4/2022 | Cass | H01R 43/24 |
| 2005/0027339 A1* | 2/2005 | Schrom | A61N 1/05 607/116 |
| 2009/0248122 A1 | 10/2009 | Pianca | |
| 2011/0054580 A1* | 3/2011 | Desai | C08G 18/698 607/116 |
| 2011/0054581 A1* | 3/2011 | Desai | C08G 18/6705 29/874 |
| 2011/0071610 A1* | 3/2011 | Shao | A61N 1/0573 607/116 |
| 2011/0118813 A1* | 5/2011 | Yang | A61N 1/05 607/116 |
| 2011/0118815 A1* | 5/2011 | Kuzma | A61N 1/0551 607/116 |
| 2011/0238145 A1 | 9/2011 | Swanson | |
| 2011/0288388 A1 | 11/2011 | Shah et al. | |
| 2012/0040547 A1* | 2/2012 | Forslund | A61N 1/056 29/876 |
| 2012/0065699 A1* | 3/2012 | Bedenbaugh | A61N 1/0534 607/45 |
| 2012/0172696 A1 | 7/2012 | Kallback et al. | |
| 2014/0018788 A1 | 1/2014 | Engelman et al. | |
| 2014/0058197 A1 | 2/2014 | Salahieh et al. | |
| 2014/0223735 A1* | 8/2014 | Shao | A61N 1/0573 29/879 |
| 2014/0343653 A1* | 11/2014 | Dollimer | H01R 43/033 607/116 |
| 2015/0100106 A1* | 4/2015 | Shishilla | A61N 1/3615 607/2 |
| 2016/0228061 A1 | 8/2016 | Kallback et al. | |
| 2016/0270732 A1 | 9/2016 | Kallback et al. | |
| 2016/0345857 A1 | 12/2016 | Jensrud et al. | |
| 2017/0056675 A1* | 3/2017 | Bortolin | A61B 5/318 |
| 2018/0008821 A1 | 1/2018 | Gonzalez et al. | |
| 2018/0117312 A1* | 5/2018 | Schmidt | A61N 1/0556 |
| 2018/0117313 A1* | 5/2018 | Schmidt | A61N 1/3752 |
| 2018/0169417 A1* | 6/2018 | Urbanski | H05K 5/0095 |
| 2019/0240019 A1* | 8/2019 | Rafiee | A61M 25/01 |
| 2019/0282805 A1* | 9/2019 | Schmidt | A61N 1/3752 |
| 2019/0374776 A1 | 12/2019 | Mishra et al. | |
| 2020/0061371 A1* | 2/2020 | Raines | A61N 1/36182 |
| 2020/0155857 A1* | 5/2020 | Lu | H05K 1/115 |
| 2020/0179678 A1* | 6/2020 | Zweber | A61N 1/37247 |
| 2020/0230425 A1* | 7/2020 | Raines | A61N 1/36125 |

* cited by examiner

LEAD BODY WITH FLEXIBLE CIRCUITS AND METHOD

CROSS-REFERENCE TO RELATED APPLICATION

This Non-Provisional Patent application claims the benefit of the filing date of U.S. Provisional Patent Application Ser. No. 62/979,564, filed Feb. 21, 2020, ENTITLED "LEAD BODY WITH FLEXIBLE CIRCUITS AND METHOD," which is incorporated herein by reference.

TECHNICAL FIELD

This disclosure relates to a high-density lead body configured for use within the body of a mammal or human.

BACKGROUND

In one case, a lead includes a lead body that couples multiple electrodes at a distal end with multiple ring electrodes at a proximal end. The electrodes are provided on the lead body and configured for sensing and/or stimulation within a biological application. In some embodiments, electrodes are provided on the distal end of a lead for sensing and/or stimulation within a human body. The distal end of a lead is placed adjacent tissue that is to be sensed or stimulated and the electrodes either transmit or receive energy. Also, respective connectors or ring contacts, which are electrically coupled to the electrodes, are provided on the proximal end of a lead for plugging in to a medical device, such as an implantable pulse generator (IPG). In some cases, it is useful to have very discrete locations energized, and accordingly, use only a segment of a ring electrode, rather than the entire ring. Accordingly, in some applications it is useful to have a large number of discrete electrode segments at the distal end coupled through the lead body to a large number of independent ring contacts at the proximal end. Manufacturing independent connections from each of the discrete electrode segments to the proximal end can be difficult, particularly where multiple electrode segments are desired on a very small diameter lead. For these and other reasons, there is a need for the disclosure.

SUMMARY

One embodiment is a method of forming a lead for implantation. The method includes forming a distal end assembly, forming a proximal end assembly, and forming a flexible circuit coupling the distal end assembly to the proximal end assembly. The distal end assembly, the proximal end assembly and the flexible circuit are formed over an inner member. An outer member is placed over the combination of the distal end assembly, the proximal end assembly and the flexible circuit. The outer member and circuit are fused adjacent the distal end assembly to the proximal end assembly.

DETAILED DESCRIPTION

In the following Detailed Description, reference is made to the accompanying drawings, which form a part hereof, and in which is shown by way of illustration specific embodiments in which the embodiments may be practiced. In this regard, directional terminology, such as "top," "bottom," "front," "back," "leading," "trailing," etc., is used with reference to the orientation of the Figure(s) being described. Because components of the embodiments can be positioned in a number of different orientations, the directional terminology is used for purposes of illustration and is in no way limiting. It is to be understood that other embodiments may be utilized and structural or logical changes may be made without departing from the scope. The following detailed description, therefore, is not to be taken in a limiting sense, and the scope is defined by the appended claims.

Figure 1:
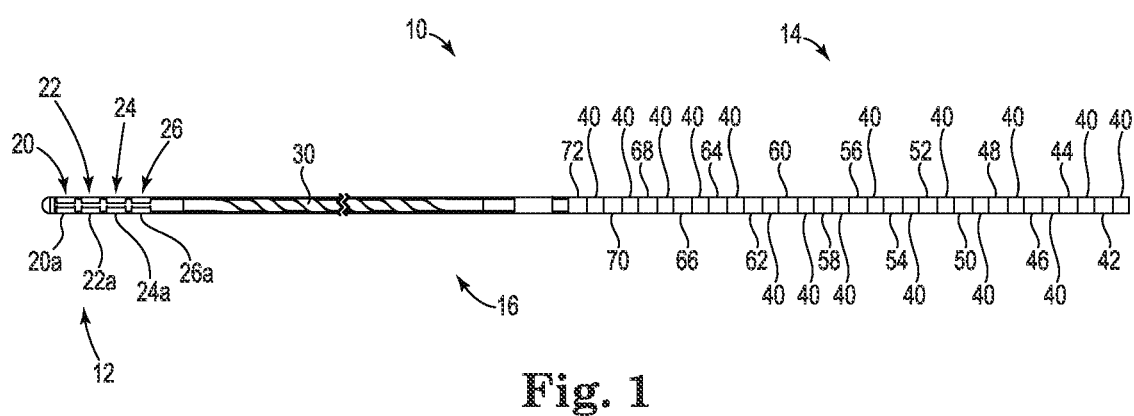
FIG. 1 illustrates a side view of a lead in accordance with one embodiment.

FIG. 1 illustrates a side view of a lead 10 in accordance with one embodiment. In one embodiment, lead 10 includes, a distal end assembly 12, a proximal end assembly 14 and a lead body 16, which in one embodiment couples the distal end assembly 12 and the proximal end assembly 14.

In one embodiment, distal end assembly 12 includes four electrodes 20, 22, 24, 26. In other embodiments, more or less electrodes may be included. In one embodiment, each of electrodes 20, 22, 24, 26 is segmented, such that each has a plurality of individually accessible electrode segments. In one embodiment, first electrode 20 includes first, second, third and fourth electrode segments 20a, 20b, 20c, and 20d; second electrode 22 includes first, second, third and fourth electrode segments 22a, 22b, 22c, and 22d; third electrode 24 includes first, second, third and fourth electrode segments 24a, 24b, 24c, and 24d; and fourth electrode 26 includes first, second, third and fourth electrode segments 26a, 26b, 26c, and 26d. In one embodiment, each electrode segment a/b/c/d of each electrode 20, 22, 24, 26 extend radially about the outer diameter of lead 10, and are each electrode segment a/b/c/d of each electrode 20, 22, 24, 26 are located along the same axial length of lead 10. Because the electrode segments are spaced radially about the circumference of lead 10, only some of the segments are visible in the side view of FIG. 1.

In various other embodiments, there can be any number of combinations of electrodes and electrode segments. For example, there can be two, three, four or five electrode segments for each of electrodes 20, 22, 24, 26. In some embodiments, some of the electrodes are single ring electrodes, without segmentation, while other of the electrodes are segmented in various combinations two, three, four or five or more segments. In some embodiments, less than four electrodes are used, and in others more than four are used.

In operation, lead 10 may be configured for use within a human body, such as within the vasculature. Once within a human body, each of electrode segments 20a/b/c/d, 22a/b/c/d, 24a/b/c/d, 26a/b/c/d may be used for directional stimulation or for positional feedback sensing. In one embodiment, rather than using a single ring electrode that spans the entire 360° circumference of the lead, lead 10 includes electrode segments 20a/b/c/d, 22a/b/c/d, 24a/b/c/d, 26a/b/

*c/d*, which only span a portion of the circumference of lead 10 (for example, 180°, 90° degrees or less), such that directional stimulation or positional feedback sensing can be much more precisely controlled relative to a given target within the human body.

In one embodiment, proximal end assembly 14 includes a number of ring contacts corresponding to the number of electrode segments. In one embodiment where there are sixteen electrode segments (20*a/b/c/d*, 22*a/b/c/d*, 24*a/b/c/d*, 26*a/b/c/d*), lead 10 includes sixteen corresponding ring contacts 42, 44, 46, 48, 50, 52, 54, 56, 58, 60, 62, 64, 66, 68, 70, 72. In other embodiments, more or fewer ring contacts may be included. In one embodiment, ring contacts 42, 44, 46, 48, 50, 52, 54, 56, 58, 60, 62, 64, 66, 68, 70, 72 are provided on the proximal end of lead 10 for plugging in to a medical device. Each ring contact 42, 44, 46, 48, 50, 52, 54, 56, 58, 60, 62, 64, 66, 68, 70, 72 is electrically isolated from each other by insulative material 40.

In one embodiment, proximal end assembly 14 is coupled with distal end assembly 12 via lead body 16, such that a medical device into which proximal end assembly 14 is plugged, either transmits or receives energy via ring contacts 42, 44, 46, 48, 50, 52, 54, 56, 58, 60, 62, 64, 66, 68, 70, 72, which are all electrically conductive and which are independently coupled to the medical device. Each of ring contacts 42, 44, 46, 48, 50, 52, 54, 56, 58, 60, 62, 64, 66, 68, 70, 72 is also coupled independently to one of electrode segments 20*a/b/c/d*, 22*a/b/c/d*, 24*a/b/c/d*, 26*a/b/c/d*, which are each proximate a location to be sensed or stimulated. Each of ring contacts 42, 44, 46, 48, 50, 52, 54, 56, 58, 60, 62, 64, 66, 68, 70, 72 is also electrically isolated from adjacent contacts by insulated portions 40.

Coupling lead body 16 between proximal end assembly 14 and distal end assembly 12, particularly when there are sixteen discrete electrical connections, is challenging. This becomes more challenging when the overall diameter of lead 10 is quite small. In one embodiment, conducting section 30 is used to complete the coupling of end assemblies 12 and 14. In FIG. 1, an outer insulative layer of lead body 16 is ghosted to reveal conducting section 30 of lead body 16. Conducting section 30 is illustrated helically extending between distal end assembly 12 and the proximal end assembly 14 of lead 10. Each electrode segment 20*a/b/c/d*, 22*a/b/c/d*, 24*a/b/c/d*, 26*a/b/c/d* has a single corresponding conducting trace within the conducting section 30, each are electrically isolated from each other, that then couples to one of ring contacts 42, 44, 46, 48, 50, 52, 54, 56, 58, 60, 62, 64, 66, 68, 70, 72.

Figure 2:
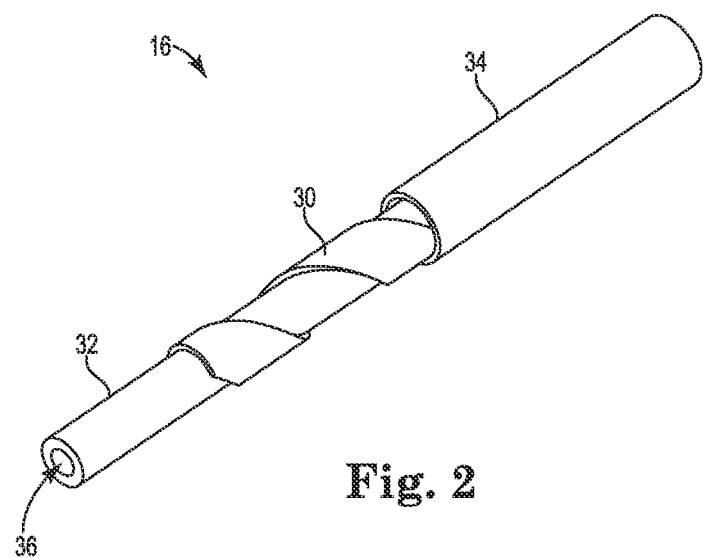
FIG. 2 illustrates a perspective view of a partially assembled lead body in accordance with one embodiment.

FIG. 2 is an isolated view of lead body 16 in accordance with one embodiment. In one embodiment, lead body 16 includes inner member 32, outer member 34 and conducting section 30. Inner member 32 provides a lumen 36, which is configured to receive a stylet or the like to assist in placement of the lead 10. In one embodiment, conducting section 30 is wrapped in a spiral or helical pattern over inner member 32. The combination of conducting section 30 over inner member 32 is this slid into outer member 34, which has in inner diameter larger than the outer diameter of conducting section 30, so that conducting section 30 and inner member 32 fit within outer member 34.

In one embodiment, conducting section 30 is a flexible circuit, such as a liquid crystal polymer (LCP) circuit. Such LCP circuit can readily carry 4, 8, 16, 32 or more independent electrical traces that electrically couple electrode segments at distal end assembly 12 to ring contacts at proximal end assembly 14. In other embodiments, conducting section 30 can be made of polyimide or silicone materials.

In one embodiment, inner member 32 and outer member 34 are flexible tubing material, such as silicone, urethane co-polymers, PTFE, ETFE, PFA and PEBAX. In one embodiment, after conducting section 30 and inner member 32 are slid within outer member 34, all three layers are heated such that the materials reflow so that the materials of each layer are bonded together along the entire length of lead body 16. Bonding along the entire length can have advantages in some applications to maximize fatigue life.

In one embodiment, rather than heating the entire length of lead body 16, only discrete locations along the length of the lead are fused. In one embodiment, only the ends of lead body 16 are heated, reflowed and fused. In this way, the non-fused portions of conducting section 30, inner member 32, and outer member 34 between the fused ends are free to move, or free float, relative to each other. This can be advantageous in applications where lead 10 is implanted within a body and subjected to twisting, bending and/or torsional forces. Allowing this relative movement or free float between the layers can help prevent kinks or breaks in the layers when subjected to these types of forces, thereby performing better than a lead body that has all layers fused together along its entire length.

Figure 3A:
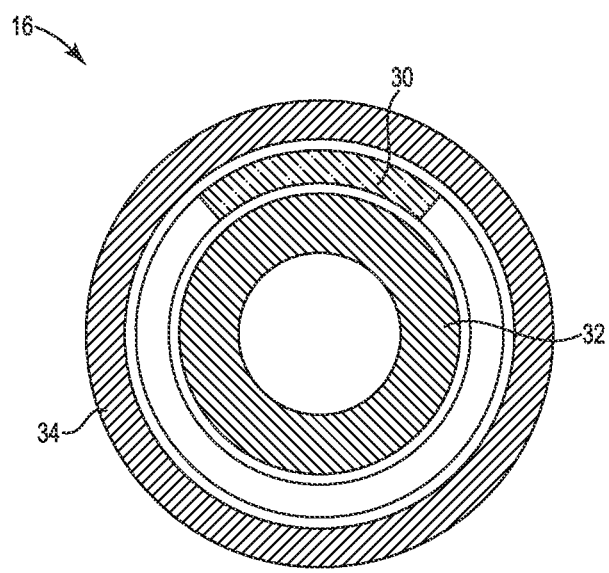
FIGS. 3a and 3b illustrate cross-sectional views of the lead body.
Figure 3B:
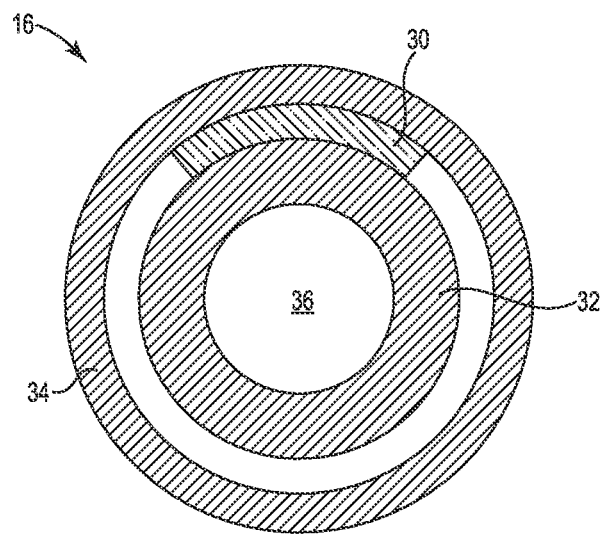

FIGS. 3*a* and 3*b* illustrate cross-sectional views of lead body 16 before and after reflowing at one of the end points along its length where the lead body 16 is heated. As illustrated in FIG. 3*a*, before the ends of lead body 16 are heated or reflowed, conducting section 30, inner member 32, and outer member 34 are free floating such that each of the layers are free to move relative to the other layers. As illustrated in FIG. 3*b*, after the ends of lead body 16 are heated or reflowed, conducting section 30, inner member 32, and outer member 34 are fused together such that conducting section 30 is pinned between inner member 32 and outer member 34 at these end locations.

Figure 4:
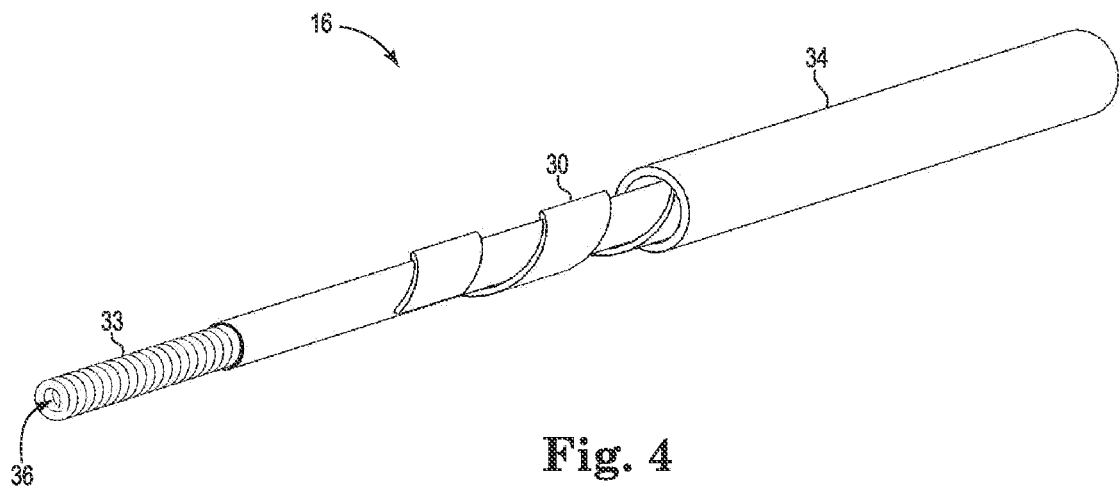
FIG. 4 illustrates a perspective view of a partially assembled lead body in accordance with one embodiment.

FIG. 4 illustrates another embodiment of lead body 16 in which conducting section 30 is helically wound over inner coil 33. Inner coil 33 provides a lumen 36, which is configured to receive a stylet or the like to assist in placement of the lead 10. The combination of conducting section 30 over inner coil 33 is this slid into outer member 34, which has in inner diameter larger than the outer diameter of conducting section 30, so that conducting section 30 and inner coil 33 fit within outer member 34.

In one embodiment, outer member 34 is a flexible tubing material, such as silicone, urethane co-polymers, PTFE, ETFE, PFA and PEBAX. In one embodiment, after conducting section 30 and inner coil 33 are slid within outer member 34, lead body 16 is heated such that the materials of outer member 34 and conducting section 30 reflow so that the materials of each layer are bonded together. In one embodiment, only the ends of lead body 16 are heated and reflowed so that the layers are free floating as discussed above.

Inner coil 33 may be made of various materials, such as MP35, Ag Core MP35, Ta-15-Molybinium, stainless steels, titanium, thermoplastics, carbon fiber, and Nitinol. While inner member 32 discussed above relative to FIG. 2 may require a lubricious coating for use with a stylet during lead 10 insertion, because inner coil 33 is made of metallic material, it does not need a lubricious coating.

Distal end assembly 12 and proximal end assembly 14 can be formed in a variety of ways consistent with embodiments. In one embodiment, distal and proximal end assemblies 12 and 14 are formed using sectioned hypotubes as described in published International Application WO 2019/033094A1 High-Density Lead Body and Method, which is incorporated by reference herein. When the distal and proximal end assemblies 12 and 14 are formed as described therein, the conducting sections from the proximal and distal ends are coupled to the conductive traces of conducting section 30 to electrically couple each of the segmented electrodes to corresponding ring contacts in lead 10.

Figure 5:
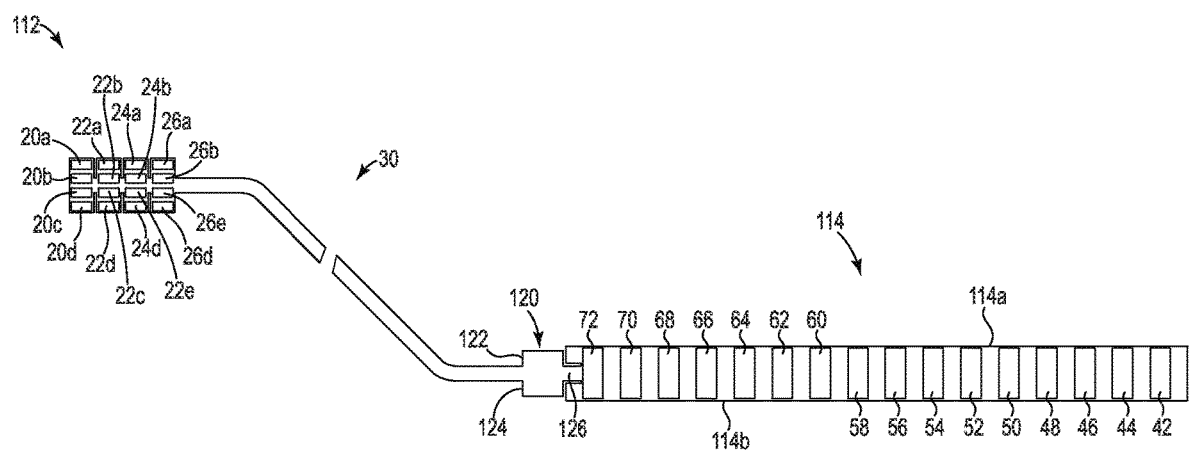
FIG. 5 illustrates a perspective view of conducting section coupled between a distal end circuit and a proximal end circuit in accordance with one embodiment.

FIG. 5 illustrates distal end circuit 112, conducting section 30 and proximal end circuit 114, each prior to being assembled into lead 10 in accordance with one embodiment. In one embodiment, each of distal end circuit 112, conducting section 30 and proximal end circuit 114 are formed on a flat flexible circuit, such as a liquid crystal polymer (LCP) circuit. In one embodiment, each of distal end circuit 112, conducting section 30 and proximal end circuit 114 are formed as a single flexible circuit, and in another embodiment, each of distal end circuit 112, conducting section 30 and proximal end circuit 114 are formed as separate assemblies and then attached together.

Because each of distal end assembly 12, lead body 16 and proximal end assembly 14 are formed on a flat flexible circuit in one embodiment, the formed conductive traces of conducting section 30 individually couple each of the sixteen electrode segments 20a/b/c/d, 22a/b/c/d, 24a/b/c/d, 26a/b/c/d to one of the corresponding sixteen ring contacts 42, 44, 46, 48, 50, 52, 54, 56, 58, 60, 62, 64, 66, 68, 70, 72 along the lead body 16.

Once each of distal end circuit 112, conducting section 30 and proximal end circuit 114 are formed on the circuit, the flat portions of distal end circuit 112 and proximal end circuit 114 can be rolled or wrapped over an inner tube, such as inner member 32 in FIG. 2, or a similar inner member, such as a mandrel. By way of this rolling, the upper edge 114a of proximal end circuit 114 abuts the lower edge 114b. In this way, rolling the flat proximal end circuit 114 over a mandrel creates proximal end assembly 14 with ring contacts 42, 44, 46, 48, 50, 52, 54, 56, 58, 60, 62, 64, 66, 68, 70, 72, as illustrated in FIG. 1. Similarly, rolling the flat distal end circuit 112 over a mandrel creates distal end assembly 12 with electrode segments 20a/b/c/d, 22a/b/c/d, 24a/b/c/d, 26a/b/c/d, as illustrated in FIG. 1.

Furthermore, in one embodiment conducting section 30 is wound or helically coiled around an inner tube, such that it creates lead body 16 substantially as illustrated in FIG. 1. In one embodiment, conducting section is first wound or helically coiled around a mandrel, and then heat-treated to form conducting section into the helically-coiled shape. The coiled conducting section 30 is then slid over an inner tube, such that it creates lead body 16 substantially as illustrated in FIG. 1. An outer tube, such as outer member 34 can also be added over the combination. As above, once the outer member 34 is added, the lead body can be fused at its ends adjacent distal end assembly 12 and proximal end assembly 14.

In one embodiment, conducting section 30 or distal end circuit 112 or proximal end circuit 114, or all three, are formed as liquid crystal polymer (LCP) circuits. In one embodiment, the circuit is create with multiple layers of LCP, which are then fused together using a thermal process. In this way, the conductive traces conducting section 30, the segmented electrodes of distal end assembly 12, and the ring contacts of proximal end assembly 14 are electrically isolated by insulating layers. Furthermore, a large number of conductive traces, segmented electrodes and ring contacts can be provided in a very small diameter lead.

In one embodiment, the melting point of the multiple layers used to form the LCP circuit are varied. For example, the outer layer of the laminate can have a higher melting point than the inner layer such that the joining of segments of the LCP circuit is optimized when they are fused or "welded" together during the thermal process.

In one embodiment, each of distal end circuit 112, conducting section 30 and proximal end circuit 114 are formed on a flat flexible LCP circuit as discrete separate parts, and then coupled together. As such, in one embodiment, conducting section 30 is provided with coupler 120. Coupler 120 has first and second shoulders 122 and 124, as well as tab portion 126. Coupler 120 is useful for securing conducting section 30 to proximal end circuit 114.

In one embodiment, conducting section 30 is narrower than is proximal end circuit 114. The relative narrow width of conducting section 30 facilitates its helical winding over inner member 32 without crowding, while the relatively larger width of proximal end circuit 114 ensures that the upper and lower edges 114a, 114b of proximal end circuit abut. However, the difference in widths between conducting section 30 and proximal end circuit 114 can make coupling them together a challenge. Accordingly, coupler 120 allows a better structure for coupling the adjacent sections.

First and second shoulders 122 and 124 give an effective width at an end of conducting section 30 that more closely approximates the width of proximal end circuit 114. Furthermore, proximal end circuit 114 is provided with a recess to receive tab portion 126, such that a more secure connection can be made between conducting section 30 and proximal end circuit 114. A similar coupler can be used to couple distal end circuit 112 as well.

Lead 10 in accordance with embodiments described herein, allow for the manufacture of leads having increased number of segmented electrodes and corresponding ring contacts, yet at the same time maintaining a very small overall diameter. Increased number of segmented electrodes and ring contacts is useful in a variety of applications. For example, lead 10 can be used in deep brain stimulation (DBS), in which lead 10 delivers electrical pulses into one or several specific sites within the brain of a patient to treat various neurological disorders, such as chronic pain, tremors, Parkinson's disease, dystonia, epilepsy, depression, obsessive-compulsive disorder, and other disorders. In other applications, lead 10 may be configured for spinal cord stimulation, peripheral nerve stimulation, dorsal root stimulation, cortical stimulation, ablation therapies, cardiac rhythm management leads, various catheter configurations for sensing, and various other therapies where directional sensing or stimulation are needed. In many such applications, a large number of ring contacts in a small diameter is very useful.

In one embodiment, the use of flexible circuit for conducting section 30 achieves decreased outer diameters of lead 10. In one embodiment, a lead with a flexible circuit for conducting section is sized with an outer diameter of 0.031 inches, making it appropriate for small animal or pediatric applications.

Although the example illustrates is 4 electrodes with 4 segments, that is, a "4×4" arrangement, other similar arrangements are readily possible, such as 2×2 (two electrodes, each with two segments), 3×3 (three electrodes, each with three segments), 4×2 (four electrodes, each with two segments), 2×3 (two electrodes, each with three segments), 3×3 (three electrodes, each with three segments), 4×3 (four electrodes, each with three segments), 2×4 (two electrodes, each with four segments), 3×4 (three electrodes, each with four segments), etc. Other configurations are readily possible, including clocked or linear electrodes, or electrodes assembled in a spiral pattern.

Figure 6:
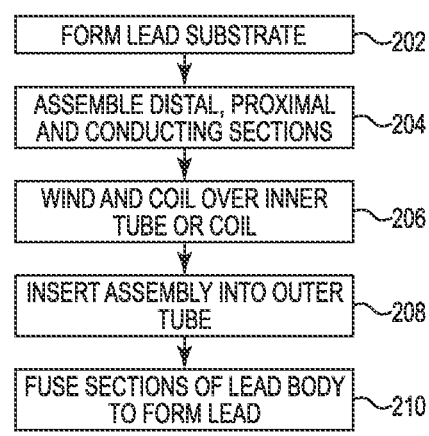
FIG. 6 illustrates a method of forming a lead with a flexible circuit in accordance with one embodiment.

FIG. 6 illustrates a method of forming a lead, such as lead 10, in accordance with one embodiment. First, at step 202, a distal end circuit, a conducting section and proximal end circuit are formed. In one embodiment, each of the distal end circuit, the conducting section and the proximal end circuit are formed on a flat flexible circuit, and in one embodiment, each are formed on a liquid crystal polymer (LCP) circuit. In one embodiment, each of the distal end circuit, the conducting section and the proximal end circuit are formed as a single flexible circuit, and in another embodiment, each are formed as separate assemblies.

At optional step 204, when the distal end circuit, the conducting section and the proximal end circuit are formed as separate assemblies, the conducting section is coupled between the distal end circuit and the proximal end circuit. In one embodiment, one or more couplers are used to couple the conducting section to the distal end circuit and/or to the proximal end circuit.

At step 206, the distal end circuit and the proximal end circuit are wound over an inner member or tube. The conducting section is helically wound over the inner member or tube. In one embodiment, the conducting section is first helically wound over a mandrel, heat-treated, and then slid over the inner member or tube.

At step 208, an outer member or tube is slid over the combination of the inner member or tube, the distal end circuit, the conducting section.

At step 210, the conducting section is fused proximate its ends, thereby forming a lead, such as illustrated in FIG. 1.

Although specific embodiments have been illustrated and described herein, it will be appreciated by those of ordinary skill in the art that a variety of alternate and/or equivalent implementations may be substituted for the specific embodiments shown and described without departing from the scope of the invention. This application is intended to cover any adaptations or variations of the specific embodiments discussed herein. Therefore, it is intended that this invention be limited only by the claims and the equivalents thereof

What is claimed is:

1. A method of forming a lead for implantation comprising:
   forming a distal end assembly;
   forming a proximal end assembly; and
   forming a flexible circuit coupling the distal end assembly to the proximal end assembly;
   wherein the distal end assembly, the proximal end assembly and the flexible circuit are formed over an inner member;
   placing an outer member over the combination of the distal end assembly, the proximal end assembly and the flexible circuit; and
   fusing both the inner member and the outer member to the flexible circuit, between the distal end assembly and the proximal end assembly at discrete locations along the lead;
   wherein fusing the inner and outer members to the flexible circuit includes reflowing the inner and outer members such that materials of the inner and outer members and the flexible circuit are bonded together along the length of the lead between the distal end assembly and the proximal end assembly, and wherein non-fused portions of the inner member and the outer member between fused ends are free to move relative to each other.

2. The method of claim 1, wherein forming one of the distal end assembly and the proximal end assembly includes forming the flexible circuit.

3. The method of claim 1, wherein forming one of the distal end assembly, the proximal end assembly, and the flexible circuit, or all three includes forming on a liquid crystal polymer (LCP) circuit.

4. The method of claim 1, wherein each of the distal end assembly, the proximal end assembly, and the flexible circuit are formed over a single connected liquid crystal polymer (LCP) circuit.

5. The method of claim 1, wherein at least one of the distal end assembly and the proximal end assembly are coupled to the flexible circuit using a coupler.

6. The method of claim 5, wherein the coupler has first and second shoulders and a tab portion.

7. A lead for implantation comprising:
   a distal end assembly;
   a proximal end assembly; and
   a flexible circuit coupling the distal end assembly to the proximal end assembly;
   wherein the distal end assembly, the proximal end assembly and the flexible circuit are formed over an inner member;
   an outer member configured over the combination of the distal end assembly, the proximal end assembly and the flexible circuit; and
   wherein the inner member and the outer member and the flexible circuit are fused together between the distal end assembly and the proximal end assembly at discrete locations along the lead; and
   wherein the inner and outer members are reflowed such that materials of the inner and outer members and flexible circuit are bonded together along the length of the lead between the distal end assembly and the proximal end assembly, and non-fused portions of the inner member and the outer member between fused ends are free to move relative to each other.

8. The lead of claim 7, wherein at least one of the distal end assembly and the proximal end assembly comprises the flexible circuit.

9. The lead of claim 7, wherein one of the distal end assembly, the proximal end assembly, and the flexible circuit, or all three, comprises a liquid crystal polymer (LCP) circuit.

10. The lead of claim 7, wherein each of the distal end assembly, the proximal end assembly, and the flexible circuit comprise a single connected liquid crystal polymer (LCP) circuit.

11. The lead of claim 7, wherein at least one of the distal end assembly and the proximal end assembly are coupled to the flexible circuit by a coupler.

12. The lead of claim 11, wherein the coupler has first and second shoulders and a tab portion.

13. The method of claim 1, wherein each of the inner member, outer member and the flexible circuit are heated such that the materials of each reflow such that the materials of each layer are bonded together along the entire length of lead body.

* * * * *